United States Patent
Archibald et al.

(10) Patent No.: US 12,017,982 B2
(45) Date of Patent: Jun. 25, 2024

(54) PROCESS FOR HYDROFORMYLATION OF OLEFINS TO ALDEHYDES

(71) Applicant: JOHNSON MATTHEY DAVY TECHNOLOGIES LIMITED, London (GB)

(72) Inventors: Fraser Robert Archibald, London (GB); Robert Arthur Jolly, London (GB); Maria del Amo Lopez, London (GB); David Keith Welch, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 325 days.

(21) Appl. No.: 17/594,435

(22) PCT Filed: May 29, 2020

(86) PCT No.: PCT/GB2020/051301
§ 371 (c)(1),
(2) Date: Oct. 15, 2021

(87) PCT Pub. No.: WO2020/240194
PCT Pub. Date: Dec. 3, 2020

(65) Prior Publication Data
US 2022/0185757 A1  Jun. 16, 2022

(30) Foreign Application Priority Data
May 30, 2019 (GB) ..................... 1907659

(51) Int. Cl.
*C07C 45/50* (2006.01)
*B01J 19/24* (2006.01)
*B01J 31/16* (2006.01)
*C07C 7/04* (2006.01)

(52) U.S. Cl.
CPC .......... *C07C 45/50* (2013.01); *B01J 19/2465* (2013.01); *B01J 31/16* (2013.01); *C07C 7/04* (2013.01); *B01J 2231/321* (2013.01); *B01J 2531/822* (2013.01)

(58) Field of Classification Search
CPC ........ C07C 45/50; B01J 31/16; B01J 19/2465
See application file for complete search history.

(56) References Cited

U.S. PATENT DOCUMENTS

| 4,148,830 A | 4/1979 | Pruett et al. |
| 5,087,763 A | 2/1992 | Sorensen |
| 6,500,991 B2 | 12/2002 | Wiese et al. |
| 8,404,903 B2 * | 3/2013 | Cox ........................ C07C 45/50 568/454 |
| 10,023,516 B2 * | 7/2018 | Brammer ............... B01J 31/185 |
| 2011/0269997 A1 | 11/2011 | Cox et al. |

FOREIGN PATENT DOCUMENTS

| CN | 102143933 B | 9/2014 |
| EP | 2297077 A1 | 3/2011 |
| JP | 2011-527287 A | 10/2011 |
| JP | 2017-537918 A | 12/2017 |
| JP | 2019-509266 A | 4/2019 |
| WO | 2016/089602 A1 | 6/2016 |
| WO | 2017/139543 A1 | 8/2017 |

OTHER PUBLICATIONS

Examination Report for Application No. GC 2020-39843, dated May 28, 2020.

* cited by examiner

*Primary Examiner* — Sikarl A Witherspoon
(74) *Attorney, Agent, or Firm* — BakerHostetler

(57) ABSTRACT

A process for the hydroformylation of olefins to aldehydes is disclosed. The process comprises: hydroformylating one or more olefins with hydrogen and carbon monoxide in the presence of a ligand-rhodium catalyst in a reaction zone; recovering a reactor effluent from the reaction zone, the reactor effluent comprising product aldehyde and the ligand-rhodium catalyst; passing the reactor effluent and a strip gas to a vaporiser, wherein the strip gas comprises carbon monoxide and is formed from a recycle strip gas stream and a make-up strip gas stream, wherein the product aldehyde is vaporised into the strip gas in the vaporiser resulting in a vapour mixture, comprising the strip gas and the product aldehyde, and a liquid mixture, comprising the ligand-rhodium catalyst; recovering the liquid mixture and recycling the ligand-rhodium catalyst to the reaction zone; recovering the vapour mixture and separating the product aldehyde from the vapour mixture.

12 Claims, 2 Drawing Sheets

PROCESS FOR HYDROFORMYLATION OF OLEFINS TO ALDEHYDES

FIELD OF THE INVENTION

The present invention relates to a process for hydroformylation of an olefin to produce an aldehyde. In particular, but not exclusively, the present invention relates to a process for hydroformylation of a $C_8$ olefin to produce a $C_9$ aldehyde. The present invention also relates to a process for hydroformylation of an olefin to produce an aldehyde using a ligand-rhodium catalyst.

BACKGROUND

The hydroformylation of olefins to produce aldehydes is performed industrially on a large scale. The aldehydes are typically intermediate products in the production of alcohols, acids or esters. A well-known process for producing such products is the LP Oxo process provided by Dow and Johnson Matthey Davy. In a typical flowsheet, for example as described in U.S. Pat. No. 4,148,830 or 5,087,763, hydroformylation is performed in the liquid phase using a ligand-rhodium catalyst. A liquid phase reactor effluent is taken from the hydroformylation reactor and fed to a catalyst separation unit where a liquid catalyst solution is separated from the product aldehyde. The liquid catalyst solution is then returned to the reactors. The liquid catalyst solution typically comprises a solvent, rhodium, a ligand, and other components present in the reactor.

Many variations of molecules that can function as a ligand are known. Commercially used ligands are often phosphines, such as triphenylphosphine; monophosphites, such as tri methylolpropanephosphite or tris(2,4-di-tert-butylphenyl)phosphite; bisphosphites; or mixtures of any of these. WO2016089602 lists various ligands. Of these 3 types of ligands, monophosphites are believed to be the most active but also to have the weakest ligand to rhodium interaction which is believed to result in a less stable catalyst complex.

A typical catalyst separation unit comprises a vaporiser in which part of the reactor effluent is vaporised. This results in a vapour phase containing the aldehyde product and essentially free of catalyst, and a liquid phase containing the liquid catalyst solution. The vapour phase is forwarded for further processing. The further processing generally includes an aldehyde purification stage, wherein unconverted olefins and paraffins are removed along with dissolved syngas and other light components. The aldehydes thus produced are typically used as intermediates for other products such as alcohols, acids or esters, which may typically be used as plasticisers.

The vaporising of the aldehyde in the reactor effluent in the catalyst separation unit is assisted by lower pressures and higher temperatures in the vaporiser. However, the liquid catalyst solution is normally sensitive to degradation of various forms resulting in loss of activity and loss of rhodium. Rhodium is a valuable precious metal and thus it is desirable for consumption of rhodium to be as low as possible in order to maintain an economical process. This often dictates the maximum allowable temperature in the vaporiser. Evaporation can still be increased by operating the vaporiser at a low pressure. Lower total pressure implies a low partial pressure of the aldehyde, which increases the evaporation of aldehyde and is particularly useful for relatively heavy aldehydes. However, a lower total pressure, and especially a vacuum, results in larger equipment volumes and thus more expensive equipment. At pressures lower than atmospheric pressure a risk also arises of air finding its way inside the process. That can result in the oxidation of the aldehyde and/or ligand, both of which result in increased costs.

It is thus desirable to stabilise the catalyst to prevent losses and desirably to permit the use of higher temperatures and above-atmospheric pressures.

U.S. Pat. No. 6,500,991 aims to stabilise the catalyst by cooling the catalyst solution obtained from the vaporiser and adding a carbon monoxide containing gas to the liquid, or by adding carbon monoxide to a flash vessel prior to the catalyst separation.

EP2297077 describes the use of a circulating strip gas in order to lower the partial pressure of the aldehyde but maintain an overall positive pressure. In the catalyst separation unit, the reactor effluent is fed to a vaporiser together with the strip gas, and both flow co-currently through the vaporiser. The strip gas is essentially free of aldehydes and thus reduces the aldehyde partial pressure in the vaporiser, thereby increasing the driving force for the aldehyde to evaporate from the reactor effluent. The vaporiser may also be heated to further stimulate evaporation. The resulting vapour mixture, comprising the aldehyde and the strip gas, is then separated from the remaining liquid catalyst solution. The liquid catalyst solution is returned to the reactor and the vapour mixture is fed to a condenser. In the condenser, the temperature of the vapour mixture is decreased with the result that essentially all the aldehyde is condensed and separated from the remaining vapour. The remaining vapour is then recompressed to the inlet pressure of the vaporiser and re-used as strip gas.

WO2016089602 describes the addition of carbon monoxide to the vaporiser strip gas in order to reduce catalyst losses. It also suggests that low hydrogen partial pressures in the strip gas can contribute to low catalyst losses. The carbon monoxide can be obtained by separating syngas into a hydrogen-containing stream and a make-up strip gas stream.

It is thought that the addition of carbon monoxide to the vaporiser strip gas results in a higher concentration of carbon monoxide in the liquid catalyst solution, and that this helps to stabilise the catalyst. However, sufficiently pure carbon monoxide is rarely available in a petrochemical facility and there is therefore a need to use syngas to produce the carbon monoxide. There remains a need for a process that provides a carbon monoxide rich gas to the vaporiser whilst minimizing the need for additional syngas feedstock.

The present invention seeks to ameliorate some of the problems with the prior art. In particular, but not exclusively, the present invention seeks to provide an improved, more cost-effective process for the hydroformylation of olefins to aldehydes.

SUMMARY OF INVENTION

According to a first aspect of the invention, there is provided a process for the hydroformylation of olefins to aldehydes, the process comprising:
  a. Hydroformylating one or more olefins with hydrogen and carbon monoxide in the presence of a ligand-rhodium catalyst in a reaction zone;
  b. Recovering a reactor effluent from the reaction zone, the reactor effluent comprising product aldehyde and the ligand-rhodium catalyst;
  c. Passing the reactor effluent and a strip gas to a vaporiser, wherein the strip gas comprises carbon monoxide and is formed from a recycle strip gas stream and a make-up strip gas stream, wherein the product aldehyde is vaporised into the strip gas in the vaporiser resulting in a vapour mixture, comprising the strip gas and the product aldehyde, and a liquid mixture, comprising the ligand-rhodium catalyst;

d. Recovering the liquid mixture and recycling the ligand-rhodium catalyst to the reaction zone;
e. Recovering the vapour mixture and separating the product aldehyde from the vapour mixture to create a product aldehyde stream and the recycle strip gas stream for returning to step (c);
f. Purging a portion of the recycle strip gas stream as a purged strip gas stream; and
g. Combining the purged strip gas stream with a hydrogen-containing stream to create a re-formed syngas stream, comprising hydrogen and carbon monoxide, and feeding the re-formed syngas stream to the reaction zone in step (a).

Thus, the invention involves a catalyst separation unit, for separating a ligand-rhodium catalyst from the effluent of a hydroformylation reaction zone, wherein a circulating strip gas is used in a vaporiser that separates the product aldehyde from the ligand-rhodium catalyst, wherein the circulating strip gas is purged, for example to prevent build-up of hydrogen and other inert components, with make-up carbon monoxide rich gas being added to the circulating strip gas, typically from a syngas separation unit. The purged strip gas, which is still rich in carbon monoxide, is combined with a hydrogen-containing stream, typically also from the syngas separation unit, to form a re-formed syngas stream that is fed to the reaction zone. Thus, the carbon monoxide comprised in the make-up strip gas stream used to create the circulating strip gas is not wasted and the overall requirement for syngas as a source of carbon monoxide is not significantly increased compared to a process in which no circulating strip gas is used. The invention thus realises the advantages of reduced ligand-rhodium catalyst losses associated with a carbon monoxide rich environment in the vaporiser, while avoiding the disadvantages of additional syngas feedstock requirements.

The make-up strip gas stream comprises carbon monoxide and is preferably rich in carbon monoxide. Preferably the make-up strip gas stream is from 50-100 mol % carbon monoxide, more preferably the make-up strip gas stream is from 70-100 mol % carbon monoxide, yet more preferably the make-up strip gas stream is from 80-100 mol % carbon monoxide, most preferably the make-up strip gas stream is from 95-100 mol % carbon monoxide. Higher concentrations of carbon monoxide are favoured as they allow for a higher concentration of carbon monoxide in the strip gas. Preferably the hydrogen-containing stream is from 50-100 mol % hydrogen, more preferably the hydrogen-containing stream is from 70-100 mol % hydrogen, yet more preferably the hydrogen-containing stream is from 80-100 mol % hydrogen, most preferably the hydrogen-containing stream is from 95-100 mol % hydrogen. In some embodiments the partial pressure of carbon monoxide in the vapour mixture leaving the vaporiser may be at least 15 psi (103 kPa) and preferably at least 20 psi (138 kPa). For example, the partial pressure of carbon monoxide in the vapour mixture leaving the vaporiser may be from at least 15 psi (103 kPa) to not more than 50 psi (345 kPa). The partial pressure of hydrogen in the vapour mixture leaving the vaporiser may, for example, be not more than 10 psi (69 kPa) and preferably not more than 5 psi (34 kPa).

Preferably the process comprises separating a syngas stream, comprising carbon monoxide and hydrogen, into the hydrogen-containing stream and the make-up strip gas stream. In effect therefore, the syngas stream is fed to the reaction zone, with the carbon monoxide in the syngas stream being fed via the strip gas in the vaporiser. That may be the only supply of syngas to the reaction zone; in other words, the re-formed syngas stream may be the only supply of syngas to the reaction zone. However, optionally, the reaction zone may be fed with the re-formed syngas stream and a fresh syngas stream. In such embodiments, for example, a syngas feed may arrive at the battery limit of the process and a portion of that syngas feed may be separated into the make-up strip gas stream and hydrogen-containing stream and a portion of that syngas feed may be fed to the reaction zone. In such cases, some of the syngas feed effectively bypasses the catalyst separation unit. Such an arrangement may be beneficial in balancing the requirements for feeding syngas to the reaction zone and carbon monoxide to the strip gas. In such embodiments however, the benefits of the invention are still realised in that carbon monoxide in the strip gas is still not wasted and is still fed to the reaction zone in the re-formed syngas stream. In such embodiments the molar ratio of the portion of the syngas feed separated into the make-up strip gas stream and the hydrogen-containing stream and the portion of the syngas feed fed to the reaction zone as the fresh syngas stream may preferably be from 0.01 to 1. More preferably the molar ratio is 0.1 to 0.5, and most preferably the molar ratio is 0.1 to 0.3. The molar ratio may be selected based on the separation efficiency, for example the membrane separation efficiency if a membrane is used for the separation, and the desired carbon monoxide partial pressure in the strip gas. For example, if the make-up strip gas stream contains a relatively high level of hydrogen, a higher flowrate of make-up strip gas stream may be used, with a correspondingly higher flowrate of the purged strip gas stream.

The molar ratio of carbon monoxide fed to the reaction zone to olefin fed to the reaction zone is preferably about 1. In practice not all the olefins will be convertible and carbon monoxide is only consumed to convert the convertible olefins. The molar ratio may therefore be less than 1 whilst still providing sufficient carbon monoxide to convert all convertible olefins. However, a molar ratio excess of carbon monoxide may be desirable for operational reasons and to enable high conversion of the more valuable olefin feedstock and a molar ratio of greater than 1 is therefore desirable. The molar ratio may preferably be between 0.1 and 10 and more preferably between 1 and 2.

The separating of the syngas stream into the hydrogen-containing stream and the make-up strip gas stream is preferably carried out using a membrane separation unit. Such membrane separation units are commercially available from companies such as MTR and Air Products. The membrane separation unit may be capable of achieving very high, such as at least 95 mol % or preferably at least 99 mol %, concentrations of carbon monoxide in the make-up strip gas stream in an economical way. Such high purities may however require a high flowrate of syngas to the membrane separation unit and it is therefore important that the carbon monoxide is not wasted. This is achieved in the present invention by the recombination of the purged strip gas stream with the hydrogen-rich stream to create the re-formed syngas stream that is passed to the reaction zone. Alternatively, or additionally, the separating of the syngas stream into the hydrogen-containing stream and the make-up strip gas stream may be carried out using the COSORB process or variations of it, such as described, for example, in *The absorption of carbon monoxide in COSORB solutions: absorption rate and capacity* J. A. Hogendoorn, W. P. M. van Swaaij, G. F. Versteeg, The Chem. Eng. Journ. 59 (1995) 243-252 or in U.S. Pat. No. 4,950,462 or in U.S. Pat. No. 5,382,417. Alternatively, or additionally, the separating of the syngas stream into the hydrogen-containing stream and the make-up strip gas stream may be carried out using low temperature absorption with liquid nitrogen.

Preferably the vaporiser is operated at a temperature of from 60 to 160° C., more preferably from 100 to 130° C. Such temperatures may help drive the vaporisation of the product aldehyde in the vaporiser. Because the process of the invention involves a high carbon monoxide partial pressure in the vaporiser, the ligand-rhodium catalyst may be stabilised, and losses prevented, even at such temperatures.

Preferably the vaporiser is operated at a pressure of from 0.1 to 2000 kPa, more preferably at a pressure from 100 to 2000 kPa and most preferably at a pressure from 100 to 300 kPa. Pressures above atmospheric pressure are particularly preferred as expensive equipment for creating a vacuum is not required and the risk of air ingress into the vaporiser is reduced.

The molar ratio of hydrogen to carbon monoxide in the syngas stream is preferably from 0.5 to 2.0. The most desirable ratio of hydrogen to carbon monoxide may depend on the desired hydrogen and carbon monoxide partial pressures in the reaction zone. Preferably the molar ratio of hydrogen to carbon monoxide in the re-formed syngas stream is similar to, for example within 10% of, the molar ratio of hydrogen to carbon monoxide in the syngas stream. It may be that the molar ratio of hydrogen to carbon monoxide in the re-formed syngas stream is preferably from 0.5 to 2.0. Hydrogen and carbon monoxide partial pressures in the reaction zone may influence the hydroformylation reaction, rate and selectivity. It may advantageously be simpler to control the partial pressures of carbon monoxide and hydrogen in the reaction zone if the molar ratio of hydrogen to carbon monoxide in the re-formed syngas stream is similar to the molar ratio of hydrogen to carbon monoxide in the syngas stream.

The vaporiser is preferably a falling film vaporiser, but may be other types of vaporiser including, for example, a vessel containing structured or random packing. The strip gas may be fed to the vaporiser in co-current or counter-current flow to the reactor effluent.

Since the recycle strip gas will be at a lower pressure than the strip gas due to pressure drops in the process, a compressor is preferably provided to compress the recycle strip gas before it is combined with the make-up strip gas. A compressor is also preferably provided to compress the re-formed syngas stream before it is fed to the reaction zone. Preferably the purged strip gas stream is purged from the recycle strip gas after the recycle strip gas is compressed. In that way, the purged strip gas stream may be at a suitable pressure for combining with the hydrogen-containing stream to form the re-formed syngas stream, which can then be compressed before feeding to the reaction zone, and separate compressors on the recycle strip gas and purged strip gas stream are avoided.

Typically, the reaction zone is operated at around 20 bar (2 MPa), for example from 15 to 25 bar (1.5 to 2.5 MPa), and the vaporiser is operated at around 1.5 bar (150 kPa), for example from 1 to 2 bar (100 to 200 kPa). However, pressures of from 50 to 235 bar (5 to 23.5 MPa) are also known for operating the reaction zone.

Preferably the olefin is a $C_2$ to $C_{16}$ olefin, more preferably a $C_4$ to $C_{12}$ olefin and most preferably a $C_8$ olefin. The olefin is preferably a mono-olefin. The olefin is preferably an acyclic olefin, for example a linear olefin or a branched olefin. For example, the olefin may be propylene or normal butene. The olefin is preferably a $C_8$ olefin however, for example octene, dimerised butene or oligomerised ethylene. Preferably the aldehyde has one more carbon than the olefin. Thus, the aldehyde is preferably a $C_3$ to $C_{17}$ aldehyde, more preferably a $C_5$ to $C_{13}$ aldehyde and most preferably a $C_9$ aldehyde. The skilled person will understand that the aldehyde produced depends on the olefin used.

The invention can be used with any suitable ligand system that benefits from a carbon monoxide enriched strip gas. Preferably the ligand is a phosphine, such as triphenylphosphine; a monophosphite, such as tri methylolpropanephosphite or tris(2,4-di-tert-butylphenyl)phosphite; a bisphosphite; or a mixture of any of these.

The reactor effluent will typically comprise further components in addition to the product aldehyde and ligand-rhodium catalyst. Such further components may include olefins and paraffins, ligand decomposition products, ligand stabilisers, aldehyde oligomers (sometime referred to as 'heavies'), water and dissolved gases. The vapour mixture leaving the vaporiser will typically comprise further components in addition to the product aldehyde and strip gas. Such further components may include olefins, paraffins and other light components. The olefins and paraffins will typically condense in the condenser, while the light components will remain in the recycle strip gas, with their levels controlled by the purging of the purged strip gas stream.

The product aldehyde stream is preferably a liquid product aldehyde stream.

The reaction zone will be understood as describing one or more hydroformylation reactors. Typically, the reaction zone will comprise one, two or three reactors. The reactors may, for example, be connected in series. Feed streams, such as the fresh syngas stream and the re-formed syngas stream, may be provided to one or more of the reactors and the reactor effluent that is passed to the vaporiser may be collected from one or more of the reactors.

Where it is said that a component, such as the product aldehyde, is vaporised, such as into the strip gas, it will be understood that a major portion of the component is so vaporised. A minor portion of the component may remain in the liquid phase, for example in equilibrium with the vaporised component in the vapour phase. It may be that at least 50 mol %, preferably at least 60 mol % and more preferably at least 70 mol % of the component is so vaporised. It may be that essentially all of the component is so vaporised. Similarly, where it is said that a component, such as the product aldehyde, is separated, such as from the vapour mixture, it will be understood that a major portion of the component is so separated. A minor portion of the component may remain. It may be that at least 75 mol %, preferably at least 90 mol % and more preferably at least 95 mol % of the component is so separated. It may be that essentially all of the component is so separated.

DESCRIPTION OF THE DRAWINGS

Embodiments of the present invention will now be described, by way of example, and not in any limitative sense, with reference to the accompanying drawings, of which.

DETAILED DESCRIPTION

Figure 1:
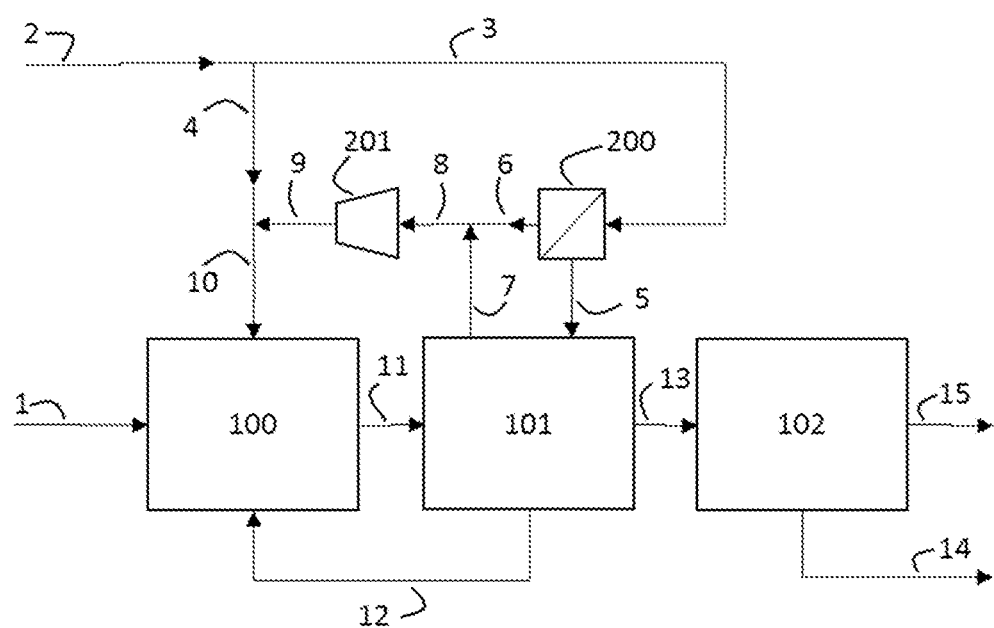
FIG. 1 is a block diagram of a flowsheet embodying the invention.

In FIG. 1 an olefin feed 1 is fed to a hydroformylation reaction zone 100. The reaction zone 100 comprises at least one reactor, and possibly two or three reactors, from which a reactor effluent 11 is passed to a catalyst separation unit 101. Liquid ligand-rhodium catalyst solution 12, with the solvent typically comprising heavies such as dimers or trimers, is recycled from the catalyst separation unit 101 to the reaction zone 100. Product aldehyde stream 13 is recovered from the catalyst separation unit 101 and passed to an aldehyde purification unit 102, from which purified aldehyde 15 is recovered. Olefins and paraffins 14 are also recovered from the aldehyde purification unit 102.

Syngas feed 2 is split into fresh syngas stream 4, which is fed directly to the reaction zone 100 as part of mixed syngas feed stream 10, and syngas stream 3, which is fed to membrane separation unit 200. In membrane separation unit 200, the syngas stream 3 is separated into make-up strip gas stream 5, which is passed to the catalyst separation unit 101, and hydrogen-containing stream 6, which is combined with purged strip gas stream 7 to form re-formed syngas stream 8, which is compressed in compressor 201 and fed 9 to the reaction zone 100 as part of mixed syngas feed stream 10. A purge may be included, for example from one or more of streams 6, 7, 8 or 9, for operational reason, but is preferably avoided so as to avoid loss of reformed syngas.

Figure 2:
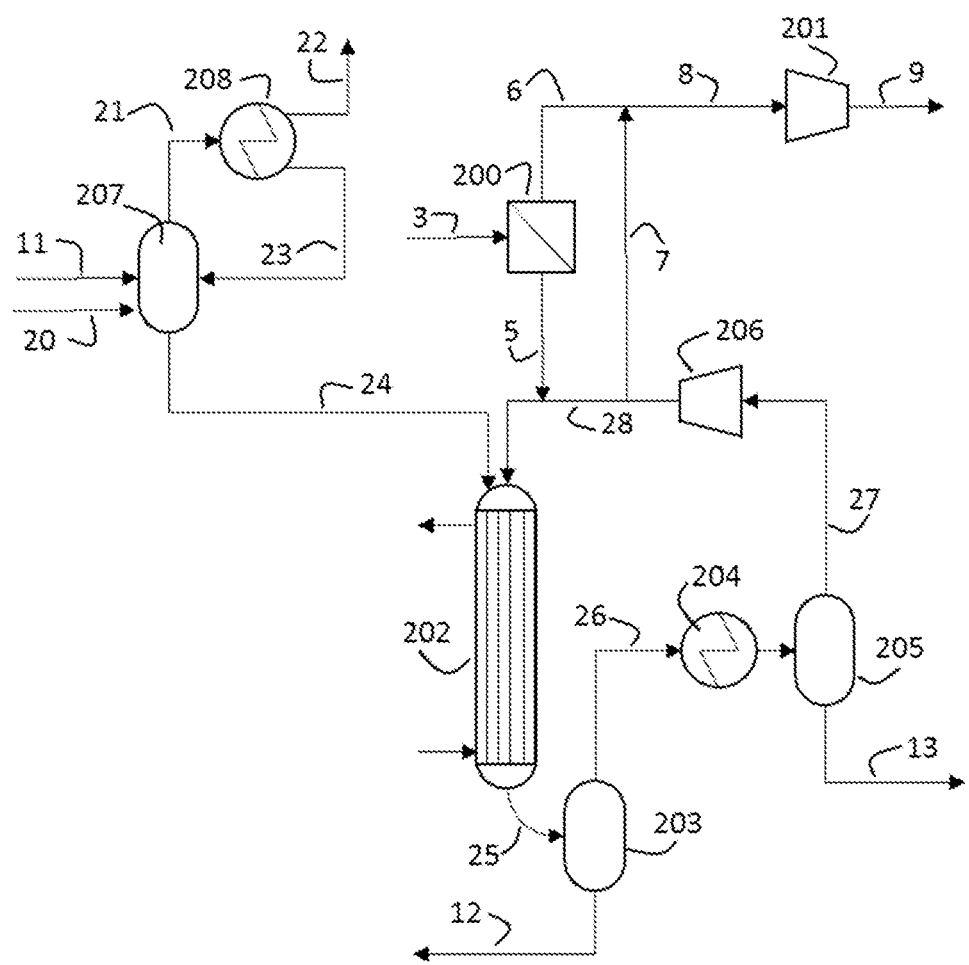
FIG. 2 is a process flow diagram of part of the process of FIG. 1 embodying the invention.

More detail of catalyst separation unit 101 is shown in FIG. 2. In FIG. 2 reactor effluent 11 and optionally a small flow of nitrogen 20, to assist stripping of hydrogen, are fed to flash vessel 207. The flash vessel 207 has a vent 21 to a condenser 208. The condenser 208 has a vent 22 and a liquid outlet stream 23, which returns to the flash vessel 207. The flash vessel 207 and condenser 208 operate to remove dissolved syngas, and especially dissolved hydrogen, from the liquid reactor effluent 11. The liquid outlet 24 from the flash vessel 207 is fed to the top of a falling film vaporiser 202 along with a strip gas 28 comprising recycle strip gas 27 and carbon-monoxide rich stream 5. Make-up strip gas stream 5 is produced by feeding syngas stream 3 to a membrane separator 200 to produce make-up strip gas stream 5 and hydrogen-containing stream 6. The outlet 25 of the vaporiser 202 is fed to a vapour/liquid separation vessel 203, from which liquid ligand-rhodium catalyst solution 12 is recovered and recycled to reaction zone 100. The vapour mixture 26 from the vapour/liquid separation vessel 203 is fed to a condenser 204 and then to a further vapour/liquid separation vessel 205. Product aldehyde stream 13 is recovered from the bottom of the further vapour/liquid separation vessel 205 and recycle strip gas 27 is recovered from the top. Recycle strip gas 27 is compressed in recycle compressor 206 before being fed back to the falling film vaporiser 202 as part of the strip gas 28. A purged strip gas stream 7 is purged from the recycle gas stream 27 after the recycle compressor 206 and combined with hydrogen-containing stream 6 to form re-formed syngas stream 8. Re-formed syngas stream 8 is compressed in syngas compressor 201 and fed 9 to the reaction zone 100. FIG. 2 has been described with a falling film vaporiser 202, but other types of vaporiser are equally applicable.

The following examples have been generated using a commercially available simulation package SimSci ProII v9.3. The use of simulations to evaluate new processes is well-established in the chemical engineering art.

Example 1

In the process of FIG. 2, 333 kmol/hr of reactor effluent 11 at 20 bara (2 MPa) and 85° C. is fed to flash vessel 207 operating at 10 bara (1 MPa), where the majority of the dissolved syngas components will flash off. Reactor effluent 11 contains mainly dissolved syngas, $C_8$ olefins, $C_8$ paraffins, $C_9$ aldehydes, and catalyst solution. A small 1 kmol/h flow of nitrogen 20 is also fed to flash vessel 207 to assist the removal of dissolved hydrogen. The vent 21 from the flash vessel 207 is fed to condenser 208 to recover the heavier $C_8$ and $C_9$ components. The liquid outlet stream 23 from the condenser 208 is returned to the flash vessel 207. The liquid outlet 24 from the flash vessel 207 is fed to the top of falling film vaporiser 202 operating at 1.5 bara (0.15 MPa). Also, strip gas 28 is fed to the top of the falling film vaporiser 202. The liquid reactor effluent and strip gas pass co-currently through the falling film vaporiser 202. The falling film vaporiser 202 is heated in order to evaporate a significant fraction of the $C_8$ and $C_9$ components. The outlet 25 of the falling film vaporiser 202 is fed to a vapour/liquid separation vessel 203. The liquid collected in vapour/liquid separation vessel 203 comprises the liquid ligand-rhodium catalyst solution 12 and a minor fraction of $C_8$ and $C_9$ components. The vapour mixture 26 from vapour/liquid separation vessel 203 is fed to condenser 204 where the majority of the $C_8$ and $C_9$ components are condensed and subsequently separated from the remaining vapour phase in further vapour/liquid separation vessel 205. The liquid thus obtained containing the $C_9$ aldehydes, olefins and paraffins, is removed from further vapour/liquid separation vessel 205 and forwarded in product aldehyde stream 13 for further processing. The vent from further vapour/liquid separation vessel 205 is recycle strip gas 27, which is fed to recycle compressor 206. The recycle compressor 206 serves to overcome the small pressure drop in the strip gas cycle. A purged recycle gas stream 7 is taken from the recycle strip gas 27 in order to maintain a constant flow rate in the strip gas loop. A make-up flow provided by make-up strip gas stream 5 is added to create strip gas 28.

A syngas stream 3 with a flowrate of 100 kmol/h syngas at 30 bara (3 MPa), with 2 mol % methane and the remainder hydrogen and carbon monoxide in a 1/1 molar ratio, is fed to the membrane separator 200. The membrane separator 200 produces, as a permeate flow, hydrogen-containing stream 6 having a flowrate of 45.6 kmol/h and, as a retentate flow, make-up strip gas stream 5. Hydrogen-containing stream 6 contains 96.77 mol % hydrogen, whilst make-up strip gas stream 5 contains 87.3 mol % carbon monoxide. The strip gas recycle flow is controlled to a constant flow of 2050 kmol/h after taking the purge of purged strip gas stream 7 and before the introduction of the make-up strip gas stream 5 as make-up. With the condenser 204 cooling to 40° C., the resulting carbon monoxide partial pressure in the strip gas 28 is 17.5 psi (120 kPa) and the hydrogen partial pressure is 2.2 psi (15 kPa). The hydrogen to carbon monoxide ratio in the re-formed syngas 8 is 0.99 mol/mol.

Example 2

As per example 1 but the syngas stream 3 flowrate is reduced to 50 kmol/h. The resulting carbon monoxide partial pressure in the strip gas 28 is now 17.0 psi (117 kPa) and the hydrogen partial pressure is 2.5 psi (17 kPa). The hydrogen to carbon monoxide ratio in the re-formed syngas 8 is 0.97 mol/mol.

Example 3

As per example 1 but the syngas stream 3 flowrate is reduced to 20 kmol/h. The resulting carbon monoxide partial pressure in the strip gas 28 is now 16.1 psi (111 kPa) and the hydrogen partial pressure is 3.2 psi (22 kPa). The hydrogen to carbon monoxide ratio in the re-formed syngas 8 is 0.93 mol/mol.

The examples demonstrate that the process of the present invention can create a high partial pressure of carbon monoxide and a low partial pressure of hydrogen in the strip gas 28, whilst still supplying a re-formed syngas 8 with a hydrogen to carbon monoxide ratio similar to that in the syngas stream 3 fed to the membrane separator 200. The carbon monoxide in the syngas stream 3 is therefore effectively used twice in the process, firstly in the strip gas 28 and then in the re-formed syngas 8 fed to the hydroformylation reaction zone. The result is that the advantages of high carbon monoxide partial pressure in the strip gas 28 are realised, while not wasting any carbon monoxide in the syngas stream 3.

It will be appreciated by persons skilled in the art that the above embodiments have been described by way of example only, and not in any limitative sense, and that various alterations and modifications are possible without departure from the scope of the invention as defined by the appended claims.

The invention claimed is:

1. A process for the hydroformylation of olefins to aldehydes, the process comprising:
   a. Hydroformylating one or more olefins with hydrogen and carbon monoxide in the presence of a ligand-rhodium catalyst in a reaction zone;
   b. Recovering a reactor effluent from the reaction zone, the reactor effluent comprising product aldehyde and the ligand-rhodium catalyst;
   c. Passing the reactor effluent and a strip gas to a vaporiser, wherein the strip gas comprises carbon monoxide and is formed from a recycle strip gas stream and a make-up strip gas stream, wherein the product aldehyde is vaporised into the strip gas in the vaporiser resulting in a vapour mixture, comprising the strip gas and the product aldehyde, and a liquid mixture, comprising the ligand-rhodium catalyst;
   d. Recovering the liquid mixture and recycling the ligand-rhodium catalyst to the reaction zone;
   e. Recovering the vapour mixture and separating the product aldehyde from the vapour mixture to create a product aldehyde stream and the recycle strip gas stream for returning to step (c);
   f. Purging a portion of the recycle strip gas as a purged strip gas stream; and
   g. Combining the purged strip gas stream with a hydrogen-containing stream to create a re-formed syngas stream, comprising hydrogen and carbon monoxide, and feeding the re-formed syngas stream to the reaction zone in step (a).

2. The process according to claim 1, wherein the make-up strip gas stream is from 50-100 mol % carbon monoxide.

3. The process according to claim 1, wherein the reaction zone is fed with the re-formed syngas stream and a fresh syngas stream.

4. The process according to claim 1, wherein the process comprises separating a syngas stream into the hydrogen-containing stream and the make-up strip gas stream.

5. The process according to claim 4, wherein the separating of the syngas stream into the hydrogen-containing stream and the make-up strip gas stream is carried out using a membrane separation unit.

6. The process according to claim 5, wherein the concentration of carbon monoxide in the make-up strip gas stream is at least 95 mol %.

7. The process according to claim 4, wherein the molar ratio of hydrogen to carbon monoxide in the syngas stream is from 0.5 to 2.0.

8. The process according to claim 4, wherein the molar ratio of hydrogen to carbon monoxide in the re-formed syngas stream is similar to the molar ratio of hydrogen to carbon monoxide in the syngas stream.

9. The process according to claim 1, wherein the vaporiser is operated at a temperature of from 60 to 160° C.

10. The process according to claim 1, wherein the vaporiser is operated at a pressure of from 0.1 to 2000 kPa.

11. The process according to claim 1, wherein the molar ratio of hydrogen to carbon monoxide in the re-formed syngas stream is from 0.5 to 2.0.

12. The process according to claim 1, wherein the olefin is a $C_2$ to $C_{16}$ olefin and the aldehyde is a $C_3$ to $C_{17}$ aldehyde.

* * * * *